United States Patent [19]
Borrebaeck

[11] Patent Number: 6,027,930
[45] Date of Patent: Feb. 22, 2000

[54] METHOD OF SELECTING SPECIFIC BACTERIOPHAGES

[75] Inventor: Carl A. K. Borrebaeck, Hjärup, Sweden

[73] Assignee: Bioinvent International AB, Lund, Sweden

[21] Appl. No.: 08/875,069

[22] PCT Filed: Jan. 15, 1996

[86] PCT No.: PCT/SE96/00030

§ 371 Date: Aug. 22, 1997

§ 102(e) Date: Aug. 22, 1997

[87] PCT Pub. No.: WO96/22393

PCT Pub. Date: Jul. 25, 1996

[30] Foreign Application Priority Data

Jan. 17, 1995 [GB] United Kingdom ............... 9500851

[51] Int. Cl.[7] .............................. C12N 7/00; C12G 1/70; C12G 1/68; G01N 33/53

[52] U.S. Cl. .................... 435/235; 435/5; 435/6; 435/7.1; 435/69.4; 536/23.4

[58] Field of Search ................. 435/5, 69.1, 7.1, 435/69.4, 252.3, 235, 6; 536/23.4

[56] References Cited

FOREIGN PATENT DOCUMENTS

0614989 A1  9/1994  European Pat. Off. .
WO 9516027  A1 9  6/1995  WIPO .

OTHER PUBLICATIONS

Duenas et al. Bio/Technology. 12(10) 999–1002, Oct. 1994.

FEMS Microbiology Letters, vol. 125, 1995, Marta Duenas et al, "Novel helper phage design: intergenic region affects the assembly of bacteriophages and the size of antibody libraries" p. 317–p.322.

Crissman and Smith, "Gene–III Protein of Filamentous Phages: Evidence for a Carboxy–Terminal Domain with a Role in Morphogenesis", Virology 132: 445–455 (1984).

Barbas III et al, "Assembly of combinatorial antibody libraries on phage surfaces: The gene III site", Proc. Natl. Acad. Sci USA 88:7978–7982 (1991).

Markland et al, "Design, construction and fuction of a multicopy display vector using fusions to the major coat protein of bacteriophage M13", Gene 109:13–19 (1991).

Primary Examiner—Paula K. Hutzell
Assistant Examiner—Lin Sun-Hoffman
Attorney, Agent, or Firm—Nixon & Vanderhye P.C.

[57] ABSTRACT

An improved method for selecting a molecule such as an antibody, antigen, peptide, protein or fragment thereof and its encoding sequence, which molecule is expressed together with a phage coat protein on the phages surface. The improvement is achieved through a new mutant filamentous helper phage which has retained the gene III promoter, whereas the gene III encoding sequence is deleted. Amplification of phage titer of $10^6$ times were achieved in M13-derived phages, when used for the selection of specific antibody.

16 Claims, 3 Drawing Sheets

METHOD OF SELECTING SPECIFIC BACTERIOPHAGES

This application represents the national phase of PCT/SE96/00030, filed Jan. 15, 1996.

TECHNICAL AREA OF INVENTION

This invention relates to the selection of specific binding proteins and their genes using a new mutant bacteriophage in phage display techniques.

BACKGROUND OF THE INVENTION

In our patent application PCT/SE94/01166 we described a method of selection of antigenic or other specific binding protein molecules, and their encoding DNA, by means of a phage display package produced by co-expression of a phagemid vector and a helper phage, in which the DNA encoding the binding peptide is inserted into the phagemid vector so as to be expressed as a fusion with a truncated phage gene III protein. The resulting display package lacks functional protein III, and is therefore not infectious, but it can be selectively rendered infectious by means of a fusion protein comprising functional protein III and the complementary binding partner for the specific binding protein present on the surface of the phage display package. The function of the helper phage is to provide the genes necessary for packaging the expression products of the phagemid; but it will be deficient in gene III so that the resulting phage display package will not contain functional gene III.

A similar system has been disclosed also in example 2 of EP-A-614989. In that case, the helper phage used was a derivative of phage Fd tet, known as fKN16, which had a deletion of 507 nucleotides in gene III. In our PCT application we used a derivative of phage M13 KO7 having a 1121 nucleotide deletion in gene III between nucleotides 1525 and 2646.

We have found that this M13 helper phage is considerably better than phage fKN16 in the performance of the procedure. Not only that, we have now also found that it is similarly better than another Fd phage (fCA55) having a larger deletion in gene III; and furthermore, that we can improve on our M13 phage construction previously described.

The experimental basis for this is presented below. In summary, however, the following general features seem to emerge.

DEFINITION OF THE INVENTION

Firstly, whereas in our original delta 3 version of the M13 helper phage, we had deleted the gene III promoter and most of the coding sequence, in our new delta 3.2 version we kept the gene III promoter but deleted effectively all the gene III coding sequence. Both constructs had the effect of preventing expression of any gene III protein, but the delta 3.2 version, by keeping the gene III promoter, retained the small intergenic (IG) region between gene VIII ligand gene III. It appears that this is at least in part responsible for the improved performance of the delta 3.2 helper phage over the delta 3 phage. Accordingly, the design of a helper phage for use in this type of selection procedure should take account of this, and substantially retain the small IG region between gene VIII and gene III.

It may not be necessary to retain the entire small IG region. This region contains a number of functional motifs. For example, as well as the promoter for gene III, there is at least one transcription termination sequence. Precisely what aspect of the small IG region is important remains to be seen, but the minimum sequence required from this region could if desired be determined by routine experimentation.

Secondly, while this development has been discovered in connection with the M13 phage, it seems likely that a similar phenomenon will be observed with other filamentous helper phages. Examples of such are fd, f1, 1f1, 1ke, ZJ/2, Xf; Ff, Pf1 and Pf3. Thus, optimal function of for example Fd-type phages in this procedure might require retention of the small IG region (along with other features).

Thirdly, insofar as retention of the small IG region involves retention also of the promoter for gene III, it is probably important that there be no gene III coding sequence, or even perhaps other coding sequence, expressible from the transcript from that promoter. This would suggest deletion of all gene III coding sequence and/or ensuring that there is no translational start codon in the transcript such as would give a protein or peptide which could interfere with the function of the helper phage and the proper packaging of the display phage.

Fourthly, as shown in FIG. 3, the M13 KO7 phage contains the kanamycin resistance gene and the p15A origin of replication inserted in the large IG region of the phage. It is believed that this too could play a significant part in the advantage which the M13 phage has over the Fd phage in the procedure of the present invention. In that case, Fd-type or other phages could be modified to incorporate an insert into the large IG region which is similar to part or all of that present in M13 KO7.

DETAILED DESCRIPTION OF THE INVENTION

The main aim of the present invention is to make available a highly efficient helper phage . It has been found that a surprisingly much more efficient selection of the phages expressing a specific binding protein or ligand I on their surface can be achieved by using a bacteriophage mutant, wherein the gene III promoter (included a small intergenic region between gene VIII and gene III) is retained, whereas gene III is deleted.

Another aspect of the invention is the use of the new mutant in a method for the improved selection of a specific binding protein or ligand I, which is expressed together with a phage coat protein on the surface of a phage characterised by, linking of specific phage replication and recognition of ligand I on the phage surface by:

a) letting a helper phage stock, which phages have kept the gene III promoter, whereas the gene III encoding sequence is deleted, but carry protein 3 on their coats, infect bacteria which comprises a phagemid vector with cloned ligand I b) adding a fusion protein between protein 3 or a part thereof and a ligand II specifically interacting with said ligand I, so that ligand I and ligand II bind specifically to each other and thereby also adding protein 3 to those specific phages which carry ligand I c) letting said phages which carry ligand I, ligand II and protein 3 on their surface infect bacteria and thereby replicate and multiply.

A further aspect of the invention is a kit comprising the new mutant.

The expression "specific binding protein" is covered by the expression "ligand I" which is represented by a peptide, a protein, an antibody or an antigen or another specific binding molecule. Ligand I is preferably an antibody and more preferably a human antibody.

"Ligand II" is a molecule such as a peptide, protein, organic molecule, hormone or other molecule specifically interacting with ligand I and capable of being linked to protein 3 in the fusion protein. Ligand I and II are thus referring to receptor-ligand pair of molecules such as antibody-antigen, hormone-receptor-hormone, growth factor-receptor-growth factor, substrate-enzyme or avidine-biotin.

The above mentioned expressions do cover functional parts thereof meaning fragments retaining the binding ability of the protein, ligand I or ligand II to about the same extent.

EXAMPLES

Figure 1:
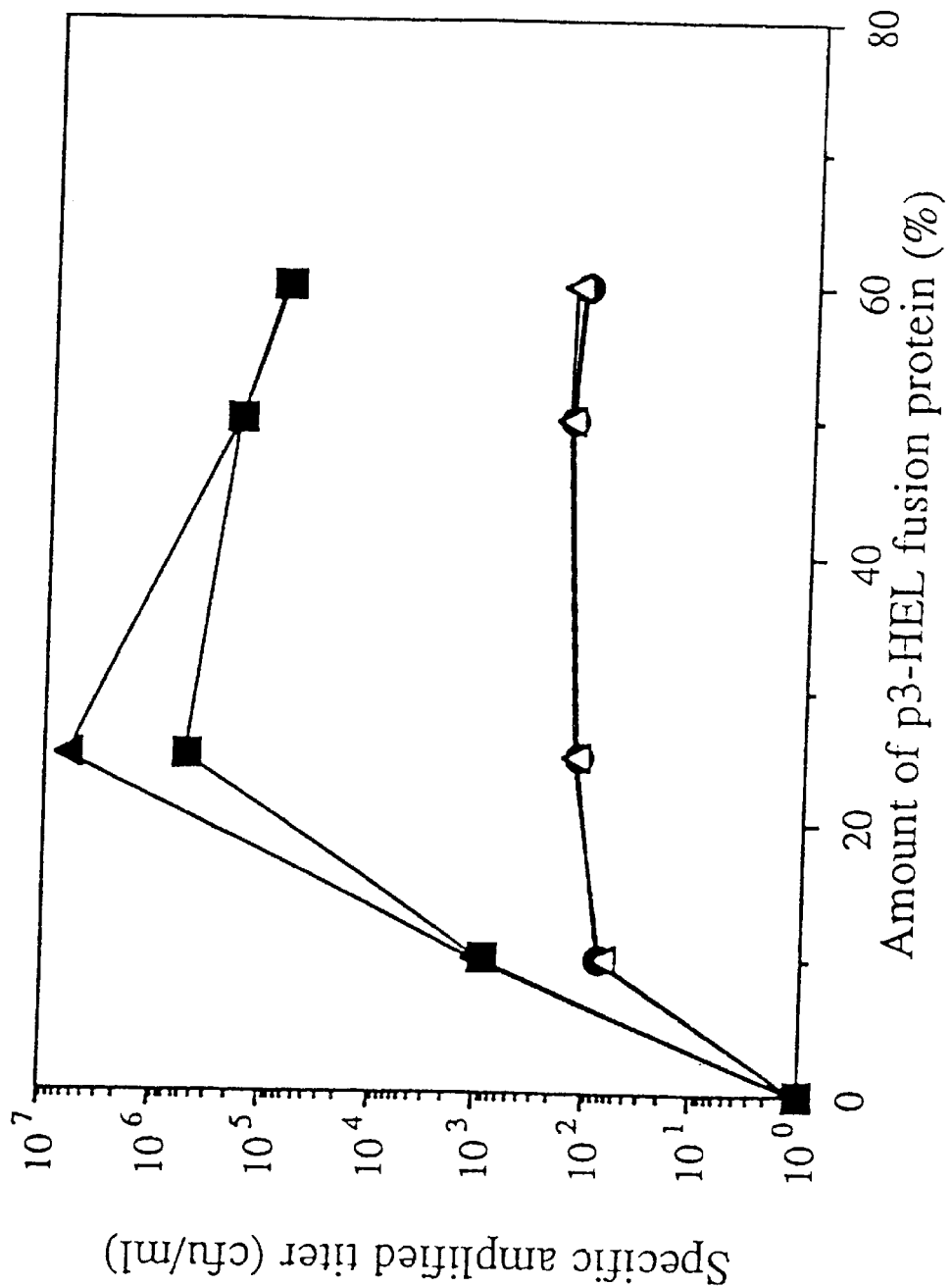
FIG. 1. PCR amplification of the deleted phages from residue 1301 to 2871, which included gene VIII and III, with the intergenic region. Lane 1: M13 KO7; Lane 2: fKN 16; Lane 3: fCA 55; Lane 4: M13MDΔ3; Lane 5: M13MDΔ3.2; Lane 6: Negative Control, Lane 7: Molecular mass markers (bp).

Phagemid vectors for display of proteins/peptides on the surface of filamentous phage utilize a plasmid genome carrying the phage origin of replication, along with the gene fused to a fragment of gene III. Generation of phage particles displaying the fusion protein also requires super-infection of the host bacterium with a helper virus. We describe here the construction of a new gene III mutant of M13 KO7 bacteriophage and compare its ability to act as helper phage with two mutants derived from Fd tet (fKN 16 and fCA 55). Furthermore, we investigate their capability to act as helper phages in SAP-selection, where non-infectious helper phage, expressing antibody fragments but not protein 3, still can infect by first reacting with a soluble antigen-protein3 fusion protein. Gene III mutants were found to be non-infectious and high titer of infective particles were obtained only when the helper phage was grown in cells harbouring a gene III-containing plasmid. Amplification of phage titer of $10^6$ times were achieved in M13-derived phages, when used for the selection of specific antibody fragments.

Introduction

Phage display of antibody fragments (1), peptides (2) and hormones (3) has been demonstrated to be a very useful technology for the rescue of specific binders from large combinatorial libraries. Two of the bacteriophage coat proteins, the major protein encoded by gene VIII (p8) and the minor protein encoded by gene III (p3), have surface-exposed N-terminal domains that tolerate foreign protein inserts and have been used to display fusion proteins. For the display of antibody fragments the p3 molecule has predominantly been used as fusion partner since only three or five copies are packed per virion. During the past five years, many improvements of the original display approach have been reported. In particular, the use of small phagemid vectors that allows packing of a mixture of wild type p3 and fusion protein has facilitated the approach.

We have recently developed a new system for selection and amplification of phages (SAP) for antibody libraries (4), in which p3-deleted, non infectious phage particles become infective by a specific interaction between the displayed antibody fragment and a soluble protein consisting of the antigen fused to the N-terminal part of p3. For this purpose we generated a mutant bacteriophage (M13MDΔ3) with a deletion in gene III and in the intergenic region (IG) between gene VIII and gene III (5). After superinfection this helper phage provided all proteins and packing signals except the wildtype p3. In the present study, we constructed and evaluated different deleted helper phages from M13 and compared these with the related Fd tet phages. We demonstrate the importance of the small IG region for correct packing and study how interference resistance of the helper phage affects the selection of phagemid particles expressing antibody fragments.

Example 1

Vector constructions, Materials and Methods

Bacterial and phage strains: *Escherichia coli* K-12 strain XL1-Blue (6) F'::Tn10proA$^+$B$^+$ lacI$^q$Δ(lacZ) M15/recA1 endA1 gyrA-96 (NAl$^r$) thi hsdR17 ($r_k^-m_k^+$) sup E44 relA1 lac and TG1 (7) F' traD36 lacI$^q$ Δ(lacZ)M15 pro A$^+$B$^+$/supE Δ(hsdM-mcrB)5($r_k^-m_k^{-McrB-}$) thi Δ (lac-proAB)were used as indicator bacteria and/or producer of bacteriophages. Bacteriophages derivated from Fd tet, the fCA 55 and fKN 16, have been described by Crissman and Smith (8), the M13 KO7 phage by Vileira and Messing (9) and the M13 MDΔ3 by Dueñas and Borrebaeck (4).

Construction of M13-derived gene III mutant: The deleted phage, denoted M13MDΔ3.2 was constructed by a complete PCR amplification of the genome of the M13 KO7 bacteriophage, excluding only gene III, thus, keeping the IG region between genes VIII and III intact. The primers used for the PCR amplification were the 5' (BamHI) CGGGATC-CATGCCAGTTCTTTG GGTA the 3' (BamHI) CGG-GATCCGTTGAAAATCTCCAAAAAAAAA GGCT the reaction was done in 30 cycles of 1 min. 94° C., 1 min. 55° C. and 9 min. 72° C. The PCR product was digested BamHI over night at 37° C. and ligated and transformed into TG1 cells containing a pUC-gIII plasmid (kindly provided by Dr. H. Hoogenboom.)

Results

Construction of M13 derived bacteriophages with a deleted gene III.

We have constructed two truncated (gene3 deleted) versions of M13 KO7 constructed and assembled by PCR. The M13MDΔ3 phage, containing a deletion of 1121 bp (from 1525 to 2646), can be used as a helper phage for superinfection if initially produced by a cell transcribing the gene III product on a separate plasmid. However, the amount of infectious particles formed was very low and only $10^5$ cfu/ml could be obtained. In order to evaluate if the small IG region between genes VIII and III was responsible for the low phage titer, we constructed a second version of the deleted M13 denoted M13MDΔ3.2. This second mutant M13 lacked only gene III, i.e.. from residue 1579 to 2851. When M13MDΔ3.2 was used as helper phage titers as high as $10^9$ cfu/ml were obtained.

Effect of gene III deletion on infectivity of M13 and Fd filamentous bacteriophages. M13MDΔ3, M13MDΔ3.2 and two derivatives of Fd tet bacteriophages (fKN 16 and fcA 55, which carried deletions of 507 and 930 bp in gene III, respectively) were used in order to examine their ability to infect *E. coli* expressing F'pili. All deletions were verified by PCR of the relevant phenotypes (FIG. 1).

The ability of both the gene III deleted M13 and Fd tet phages to infect F'$^+$ *E. coli* (TG1 or XL1-Blue) strains grown in tetracycline, was abolished. However, when these phages were produced in bacteria harbouring a pUC-gIII plasmid, which provided p3 in a transcomplementation to the phage particle, the non-infectious phenotype was overcome by the presence of p3 in the viral coat. However, only the deleted genome was incorporated into the phage, since the pUC-gIII plasmid does not carry the filamentous phage origin of replication and packing signals. The progeny phages were thus able to infect only once since non-infectious particles were subsequently assembled. Table I shows the yield of infectious particles obtained with or without the co-expression of p3. Even though the infectivity of all mutant phages was restored by incorporating p3, not all of them were efficiently assembled. The M13MDΔ3 phage formed only $10^5$ cfu/ml in contrast to M13MDΔ3.2, which was assembled simliarily to the fCA 55 phage.

Example 2
Helper Phage, fusion protein and SAP-selection

Helper phage and noninfective phage stocks were prepared as described (4), using the four mutant helper phages derived from M13 and Fd, tet. of Example 1. Briefly, *E. coli* containing a plasmid carrying gene III were transformed with the differently deleted bacteriophages. After over night incubation the supernatant containing the helper phages was titrated using XL1-Blue as indicator bacteria. Cells harbouring a phagemid encoding for anti-hen egg lysozyme (HEL) or anti-phenyloxazolone Fab fragments, fused with the carboxy-terminal part of p3, were infected with the mutant helper phages, thus, creating non-infectious phage stocks. A gene coding for HEL and a 98 amino acid fragment of M13 p3 was assembled by PCR, using the primers described in (4) and cloned into a pUC19-based plasmid. The fusion protein was expressed as a soluble periplasmic protein. The characterization of the fusion protein as a bridging molecule and the SAP procedure was performed, as previously described. (4). The specific amplification was determined as the increase in titer of the anti-HEL phage preparation over the non-specific anti-phenyloxazolone, using different amounts of fusion protein. The amount of fusion protein is given in % (v/v).

Example 3
Comparison of mutant phages in SAP selection

Figure 2:
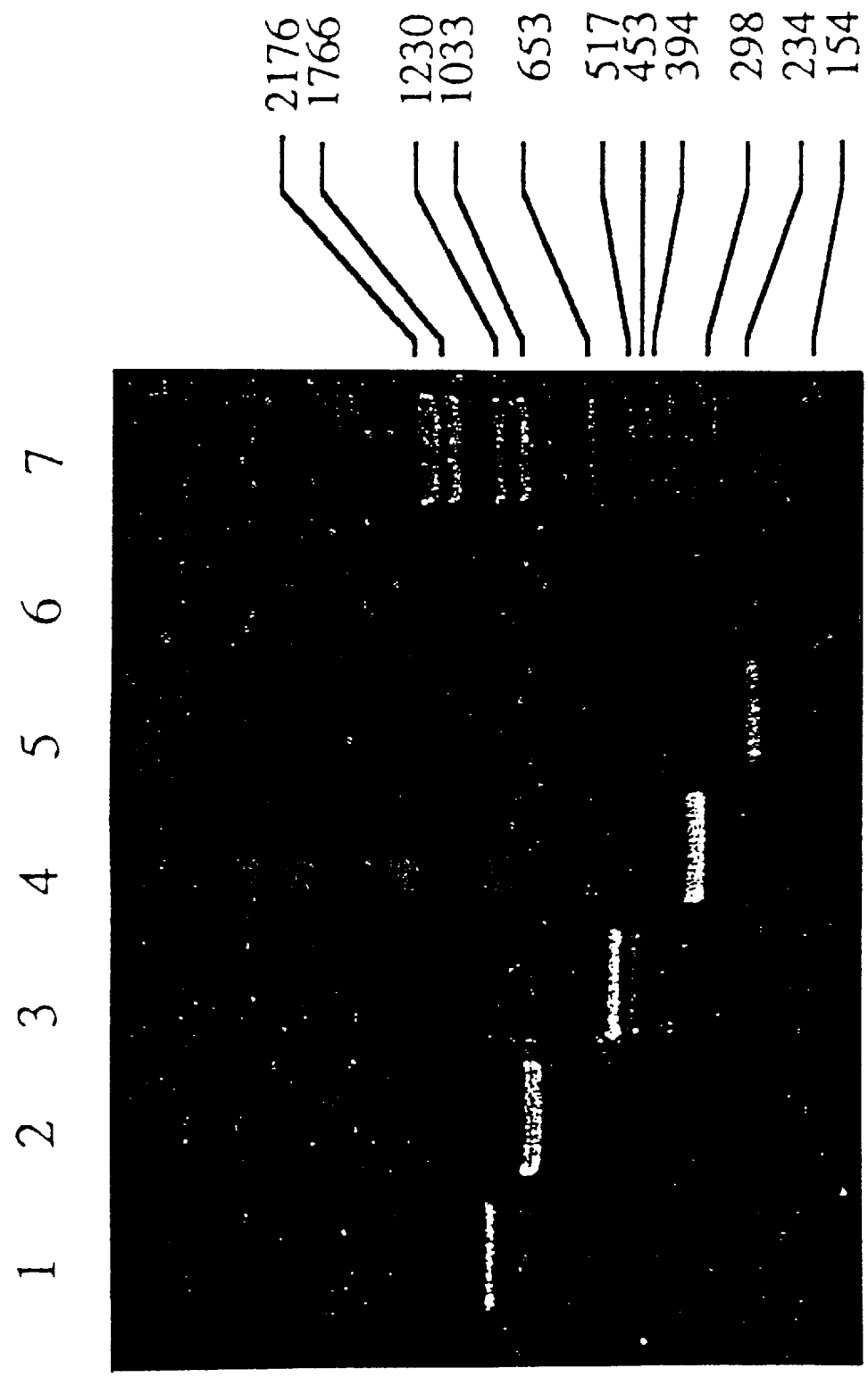
FIG. 2. Selection and amplification of phages (SAP) using the four helper phage constructs for phagemid particle preparation. The values represent the mean of three different experiments. (●) fKN 16, (Δ) fCA 55, (■) M13 MDΔ3 and (▲) M13 MDΔ3.2.
Figure 3:
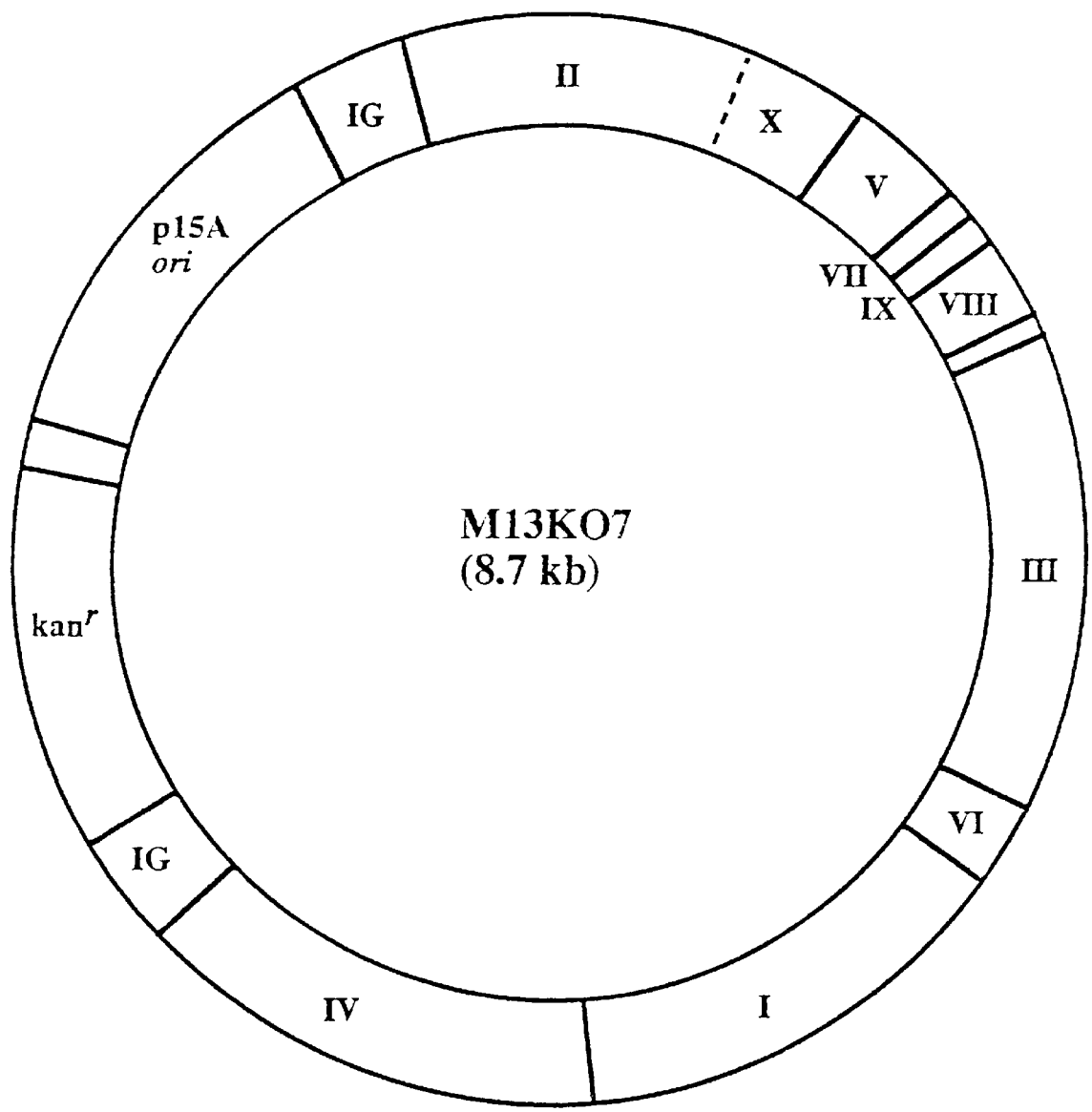
FIG. 3. The genetic map of the vector M13KO7 (Vieira and Messing 1987).

Phagemid stocks were prepared displaying antibody Fab fragments specific for HEL and phenyloxazolone. These were specifically amplified and selected using a HEL-p3 fusion protein as a bridging molecule between the F'pili and the non-infectious phagemid particle (4). Different dilutions of the fusion protein were used and the phage titers are shown in FIG. 2. M13MDΔ3 and M13MDΔ3.2 yielded a specific phage amplification of $5\times10^5$ and $2\times10^6$-fold, respectively, whereas the Fd-derived phages only gave 100-fold amplification over a high background of non specific infections. High concentrations of the fusion protein (above 30%) caused an inhibitory effect most probably due to a depolymerization of the bacterial pili by the p3 fragment, thus, limiting the infection process.

Discussion

Previous studies have shown that non-polar mutants of gene III of M13 (10) or Fd tet (8) produced defective phage particles and accordingly ascribed two functions to the gene III product: infectivity and normal (non-polyphage) morphogenesis. The finding that the fKN 16 phage could not infect via F'pili, but still retained its ability to form normal particles, suggested that the intact carboxy-terminal domain allows it to carry out the morphogenic function of p3 (8). We constructed and evaluated two non-polar mutants of M13 KO7, where the coexpression with recombinant p3 allowed generation of "normal" particles. The first construction, carrying a deletion comprising the small intergenic region between gene VIII and gene III, did not pack efficiently which resulted in a $10^4$-fold reduction in phage titer, as compared to wildtype M13 KO7. This non-coding region contains the central terminator of transcription (5). This was shown by analysis of in vitro transcripts coupled to transcription-translation, where initiation occur at nine different sites along the viral genome but, in absence of rho, all in vitro transcripts terminated at this unique terminator site (11). Also, this region contains the promoter preceding gene III, that can generate differences in the amount of gene VI, I and IV transcripts. Consequently the M13MDΔ3.2 helper phage was constructed where the IG region was kept intact. The dramatic increase in titers of infectious particles might be due to the generation of normal levels of mRNA coding for protein I, IV or VI, which have been shown to be important for the correct assembly of phage particle. Since it has been reported that gene III mutants of the Fd tet phage were more likely to tolerate aberrations in gene III without killing its host than wild type M13 (12), we compared our constructions with the fd-derived mutants fKN and fCA 55. The data showed that we indeed could obtain similar titers of Fd tet as compared to non-deleted M13 helper phage.

However, to be useful as a helper phage when constructing antibody libraries, non-interference of the assembly and capability to be rescued after antigenic selection was needed. It was obvious that only the M13 KO7 derivatives that had been engineered to interference resistance by introducing a selection marker and origin of replication between the two domains of the IG region and protein 2 overexpression (9) were able to produce a high yield of phages when they were selected and amplified with the fusion protein. Thus, efficient assembly of the foreign DNA (i.e. the phagemid vector) into phage particles depended on its preferential packing over the phage genome.

In summary, we can conclude that M13-derived mutant bacteriophages could be efficiently used as helper phages in a method for the selection and amplification of a specific binding protein and preferably in the SAP selection and that the IG region between gene VIII and gene III was needed for an efficient assembly of the phage particle.

References

1. Griffiths, A. D. (1993) Production of human antibodies using bacteriophage. Curr. Opinion Immunol 5, 263–267.
2. Lane, D. P. and Stephen, C. W. (1993) Epitope mapping using bacteriophage in peptide libraries. curr. Opinion Immunol. 5, 268–271.
3. Bass, S., Geene, R. and Wells, J. A. (1990) Hormone Phage: An enrichment method for variant proteins with altered binding properties. Proteins 8, 309–314.
4. Dueñas, M. and Borrebaeck, C. A. K. (1994) Clonal selection and amplification of phage displayed antibodies by linking antigenic recognition and phage replication. Bio/Technology 12, 999–1002.
5. Wezenbeck, P. M., G. F., Huselbos, T. J. M. and Schoenmarker, G. G. (1980) Nucleotide sequence of filamentous bacteriophage M13 DNA genome: comparison with phage fd. Gene 11, 129–148.
6. Bullock, W. O., Fernandez, J. M. and Short, J. M. (1987) XL1 Blue: A high efficiency plasmid transforming recA *E. coli* strain with beta-galactosidase selection. Bio Techniques 5, 376–379.
7. Gibson, T. J. (1984) Estudies on the Epstein Barr virus genome. Ph.D. Thesis. Cambridge University, England.
8. Crissman, J. W. and Smith, G. P. (1984) Gene III protein of filamentous phages: Evidence for a carboxylterminal domain with a role in morphogenesis. Virology 132, 445–455.

9. Vieira, J. and Messing, J. (1987) Production of single-stranded plasmid DNA. Methods Enzymol. 153, 3–11.
10. Pratt, D., Tzagoloff, H. and Beaudoin, J. (1969) Conditional lethal mutants of the small filamentous coliphage M13. Two genes for coat proteins. Virology 39, 42–53.
11. Konings, R. N. H. and Schoenmarkers, J. G. G. (1978) Transcription of the filamentous phage genome in Single-stranded DNA Phages (Denhardt, D. T., Ray, D. S. and Dressler, E., Eds.), pp. 507–530. Cold Spring Harbor Laboratory, Cold Spring Harbor, N.Y.
12. Smith, G. P. (1988) Filamentous phage assembly: morphogenetically defective mutants that do not kill the host. Virology 167, 156–165.

TABLE 1

Effect of co-expression of protein 3 on the helper phage titer (cfu/ml).

| PHAGE | TG1 | TG1 + GIII | XL1 Blue | XL1 Blue + GIII |
|---|---|---|---|---|
| M13 KO7 | $3 \times 10^{11}$ | $5 \times 10^9$ | $1 \times 10^{11}$ | $8 \times 10^8$ |
| fKN 16 | $3 \times 10^4$ | $2 \times 10^{10}$ | ND | ND |
| fCA 55 | $<10^2$ | $5 \times 10^8$ | ND | ND |
| M13 MDΔ3 | $<10^2$ | $4 \times 10^5$ | $<10^2$ | $2 \times 10^5$ |
| M13 MDΔ3.2 | $<10^2$ | $3 \times 10^8$ | $<10^2$ | $2 \times 10^9$ |

ND = No determined.

I claim:

1. A bacteriophage with improved efficiency as a helper phage in the selection and amplification of a nucleic acid encoding a specific binding protein, or a binding functional part thereof, characterised in that
a gene III promoter is kept, whereas the gene III coding sequence is deleted.

2. The bacteriophage as claimed in claim 1, wherein said bacteriophage is a mutant of a filamentous bacteriophage selected from the group consisting of M13, fd, f1, 1f1, lke, ZJ/2, Xf, Ff, Pf1 and Pf3.

3. The bacteriophage according to claim 1, wherein said bacteriophage is a mutant of the bacteriophage M13 in which an intergenic region between gene VIII and gene III is retained.

4. The bacteriophage according to claim 1, wherein the bacteriophage is the mutant M13MDΔ3.2 of the bacteriophage M13 KO7.

5. A method for the improved selection of a ligand I, which is expressed together with a phage coat protein on the surface of a phage characterized by, linking of specific phage replication and recognizing of ligand I on the phage surface comprising the steps of:
   a) letting a helper phage stock, which phages have kept the gene III promoter, whereas the gene III coding sequence is deleted, but carry protein 3 on their coats, infect bacteria which comprises a phagemid vector encoding cloned ligand I
   b) adding a fusion protein comprising protein 3 or a part thereof capable of mediating infection of said bacteria and a ligand II specifically interacting with said ligand I, so that ligand I and ligand II bind specifically to each other and thereby also adding protein 3 to those specific phages which carry ligand I
   c) letting said phages which carry ligand I, ligand II and protein 3 on their surface infect bacteria and thereby replicate and multiply.

6. A method according to claim 5 characterised in that ligand I is selected from the group consisting of peptide, protein, antibody, antigen and fragments thereof.

7. A method according to claim 5, characterized in that ligand II is selected from the group consisting of peptide, protein, organic molecule, hormone and other molecule which interacts specifically with ligand I and is linked to protein 3 in the fusion protein.

8. A method according to claim 5, characterized in using a human antibody or functional fragment thereof as ligand I on the phage surface.

9. A kit for the improved selection and amplification of nucleic acid encoding a ligand I comprising:
at least
   a) a helper phage stock, which phages have kept the gene III promoter whereas a gene III coding sequence is deleted, but which carry protein 3 on their coats enabling them to infect a bacteria host once
and optionally
   b) a bacteria which comprises a phagemid vector with cloned ligand I and/or
   c) a fusion protein comprising protein 3 or a part thereof and a ligand II specifically interacting with said ligand I expressed on the bacteria surface
and/or
   d) a bacteria capable of being infected by the phages which carry ligand I, ligand II and protein 3 on their surface and thereby replicate and multiply in said bacteria.

10. A kit according to claim 9, wherein said helper phage is a mutant of a filamentous bacteriophage selected from the group consisting of M13, fd, f1, 1f1, 1ke, ZJ/2, Xf, Ff, Pf1 and Pf3.

11. A kit, according to claim 9, wherein said helper phage is a mutant M13MDΔ3.2.

12. A method for the improved selection of a specific binding protein or ligand I, which is expressed together with a phage coat protein on the surface of a phage characterized by, linking of specific phage replication and recognition of ligand I on the phage surface comprising the steps of:
   a) letting a helper phage stock, comprising bacteriophage according to claim 1, which phages have kept the gene III promoter, whereas the gene III coding sequence is deleted, but carry protein 3 on their coats, infect bacteria which comprises a phagemid vector with cloned ligand I
   b) adding a fusion protein comprising protein 3 or a part thereof and a ligand II specifically interacting with said ligand I, so that ligand I and ligand II bind specifically to each other and thereby also adding protein 3 to those specific phages which carry ligand I
   c) letting said phages which carry ligand I, ligand II and protein 3 on their surface infect bacteria and thereby replicate and multiply.

13. A method according to claim 12 characterized in that ligand I is selected from the group consisting of peptide, protein, antibody, antigen and fragments thereof.

14. A method according to claim 12, characterized in that ligand II is selected from the group consisting of peptide, protein or fragment thereof, organic molecule, hormone and other molecule which interacts specifically with ligand I and is linked to protein 3 in the fusion protein.

15. A method according to claim 12, characterized in using a human antibody or functional fragment thereof as ligand I on the phage surface.

16. The kit according to claim 9 wherein said helper phage is a mutant of the bacteriophage M13 in which an intergenic region between gene VIII and gene III is retained.

* * * * *